(12) United States Patent
Malczewski et al.

(10) Patent No.: US 7,390,346 B2
(45) Date of Patent: Jun. 24, 2008

(54) SYSTEM AND APPARATUS FOR PRODUCING PRIMARY STANDARD GAS MIXTURES

(75) Inventors: Mark Leonard Malczewski, North Tonawanda, NY (US); Douglas Charles Heiderman, Akron, NY (US)

(73) Assignee: Praxair Technology, Inc., Danbury, CT (US)

( * ) Notice: Subject to any disclaimer, the term of this patent is extended or adjusted under 35 U.S.C. 154(b) by 517 days.

(21) Appl. No.: 11/127,144

(22) Filed: May 12, 2005

(65) Prior Publication Data

US 2006/0254656 A1  Nov. 16, 2006

(51) Int. Cl.
  *B01D 53/22* (2006.01)
  *G01N 1/00* (2006.01)
(52) U.S. Cl. .................. 95/45; 95/1; 95/47; 95/48; 95/49; 95/50; 95/51; 96/4; 96/424; 141/2; 141/4; 141/47; 141/197; 73/1.03; 436/8; 436/9; 137/624.11
(58) Field of Classification Search .......... 95/1, 95/45, 47, 48, 49, 50, 51; 96/4, 424; 141/2, 141/4, 47, 49, 83, 100, 197; 137/3, 7, 624.11; 73/1.03, 1.06, 31.03; 436/8, 9
  See application file for complete search history.

(56) References Cited

U.S. PATENT DOCUMENTS

| | | | | |
|---|---|---|---|---|
| 3,854,894 A * | 12/1974 | Klass et al. | ...................... | 137/3 |
| 3,997,296 A * | 12/1976 | Miller | ............................ | 436/8 |
| 4,335,073 A * | 6/1982 | Sherwood et al. | ........... | 73/31.05 |
| 4,388,272 A * | 6/1983 | Gesteland | .................... | 73/1.05 |
| 5,214,952 A | 6/1993 | Leggett et al. | .................... | 73/1 |
| 5,239,856 A * | 8/1993 | Mettes et al. | ................. | 73/1.05 |
| 5,583,282 A * | 12/1996 | Tom | ........................... | 73/1.06 |
| 5,648,603 A * | 7/1997 | Hanson | .................... | 73/152.02 |
| 5,661,225 A | 8/1997 | Ridgeway et al. | ............ | 73/1.06 |
| 6,000,275 A * | 12/1999 | Nishina et al. | ................ | 73/1.05 |
| 6,376,249 B1 * | 4/2002 | Adachi et al. | ................... | 436/8 |
| 6,997,347 B2 * | 2/2006 | Peng et al. | .................... | 73/1.04 |

OTHER PUBLICATIONS

Nelson, Gary O., "Gas Mixtures Preperation and Control", Lewis Publishers. 1992.*
Nelson, "Gas Mixtures and Preparation and Control", Lewis Publishers (1992).

* cited by examiner

*Primary Examiner*—Jason M Greene
(74) *Attorney, Agent, or Firm*—Iurie A. Schwartz

(57) ABSTRACT

Provided is a novel system and apparatus for producing primary standard gas mixtures. The system includes providing a gas permeation device having a constant diffusion rate into a temperature controlled enclosure; connecting a supply source of a component to the permeation device; routing the component from the gas permeation device to a product container until a desired amount of said component in the product container is reached; and supplying a balance of purified gas to the product container to obtain a known concentration of component in the primary standard gas mixture.

13 Claims, 1 Drawing Sheet

Use of Permeation Tube for NO Mixture Making

SYSTEM AND APPARATUS FOR PRODUCING PRIMARY STANDARD GAS MIXTURES

BACKGROUND OF THE INVENTION

1. Field of the Invention

The present invention relates to a system and apparatus for the preparation of low concentration primary standard mixes. The standard mixes of the present invention are utilized for calibrating analytical detectors, such as mass spectrometers, and for analysis of emissions from combustion chambers and process tools.

2. Description of Related Art

The demand for low concentration primary standard gas mixtures in the range of (100-1000 parts per billion (ppb)), is increasing in a number of industries. Of particular interest for environmental emissions testing is a mixture of nitric oxide in nitrogen, as environmental regulations become increasingly strict.

The need for supplying gas with UHP purity levels has led the industry to develop analytical techniques for measuring gas impurities. Advances in gas analysis instrumentation in the same range of impurities as would be found in typical gas analysis instrumentation has led to increase demand for low concentration primary standard mixes employed as calibration gases.

Currently, low concentration primary mixes are prepared by two methods as described by G.O. Nelson, *Gas Mixtures Preparation and Control*, Lewis Publishers, Ann Arbor, Mich. (1992). One is a static mixture, where a volume of the desired mixture is generated and then contained in a cylinder at either low or high pressures. The mixture is subsequently utilized for the particular application. Another is the dynamic mixture where the components of interest are introduced into a stream of purified diluent gas at essentially atmospheric pressure, and the desired concentration is generated. The mixture is thereafter consumed as a calibration gas for an analytical instrument.

Over the years a number of methods have been devised to control the dynamic addition of the components of interest to the diluent gas. In this regard, Leggett et al in U.S. Pat. No. 5,214,952 discloses a calibration device utilizing a series of highly accurate mass flow controllers to provide rapid delivery of ultra high calibration gas mixtures, and sample gas, to a gas analyzer at elevated temperatures.

Ridgeway et al in U.S. Pat. No 5,661,225 discloses a system for the dynamic dilution of a high concentration analyte containing gas for calibrating analytical detectors. The calibration systems described in Leggett et al and Ridgeway et al include permeation tubes and mass flow controllers for the dynamic addition of the components of interest to the diluent gas.

Some of the drawbacks associated with the static mixture related art includes the number of sequential dilutions necessary for each component added to arrive at the standard gas mixture. For example, the uncertainty in the final concentration increases with the number of dilutions. As such, in the related art it is necessary to have a minimum of three dilutions to generate a primary standard at concentrations below one part per million. Multiple dilutions can also deleteriously contribute to the contamination of the process as exposure to the ambient atmosphere is increased. In addition, the multiple dilution method requires considerable capital expenditure, as a skilled operator is required to monitor and intervene in the process.

To overcome the disadvantages of the related art, it is an object of this invention to provide a system and apparatus for producing static mixtures of low concentration (i.e., 10 ppb to 1000 ppb) primary standard mixtures.

It is another object of this invention, to utilize a permeation device, as a precise metering device to dispense minor components directly into a cylinder for a predetermined period of time, thereby allowing to weight traceable back to a National Institute of Standards Technology (NIST) standard.

Other objects and aspects of the present invention will become apparent to one skilled in the art on a review of the specification and claims appended hereto.

SUMMARY OF THE INVENTION

The foregoing objectives are met by the system and apparatus for the present invention for producing primary standard mixtures.

According to a first aspect of the invention, a system for producing primary standard gas mixtures is provided.

The system includes providing a gas permeation device having constant diffusion rate into a temperature controlled enclosure; connecting a supply source of a component to the permeation device; routing the component from the gas permeation device to a product container until a desired amount of said component in the product container is reached; and supplying a balance of purified gas to the product container to obtain a known concentration of component in the standard gas mixture.

According to a second aspect of the invention, system for producing standard gas mixture is provided. The system includes providing an ultra high purity source for a gaseous component; communicating the gaseous component via a conduit to a permeation device disposed in a temperature controlled enclosure; diffusing the gaseous component through the permeation device and removing diffused component therefrom; delivering for a predetermined period of time the diffused component to a product cylinder via a conduit; and upon reaching the set point a balance of purified gas is delivered from a high pressure source to the product container in order to obtain a known concentration of component in the standard gas mixture.

According to another aspect of the invention an apparatus for producing primary standard gas mixtures is provided. The apparatus includes a gas permeation device having constant diffusion rate disposed in a temperature controlled enclosure; a supply source in communication with the gas permeation device to provide a component; a product container to receive the liquid or gaseous component from the gas permeation device; and a supply source of purified gas in communication to the product container to supply the balance of the gas and obtain a known concentration of component in the standard gas.

BRIEF DESCRIPTION OF THE FIGURES

The invention will be better understood by reference to the following figures, wherein.

DETAILED DESCRIPTION OF THE INVENTION

The objects of the invention are accomplished using a system and apparatus which provides a single step preparation of a static primary standard gas mixture with minimal operator intervention. The system employs a gas permeation device having a diffusion rate which can be controlled to stay within a range, around a constant set point.

The system is designed to produce such calibrating standard in the form of a low concentration calibration gas mixture of the desired carrier gas or diluent, generally in ultra high purity form, and a doped quantity of the appropriate impurity or analyte, generally provided as a liquid or gaseous component, for purposes of calibrating analytical instruments. As herein utilized, the terms "carrier gas", "diluent", "purified gas" and "purified carrier gas" are utilized interchangeably to refer to the balance gas employed in generating the primary standard gas mixture. Likewise, the terms "analyte" and "impurity" are employed interchangeably to refer to the liquid or gaseous component added to generate the calibrated standard gas mixture. Calibration equipment is used to certify the purity of chemicals used to meet the requirements of the electronics industry, or to monitor the emissions from semiconductor processing equipment, automobiles, chemical and process industries. The low concentration of the liquid or gaseous component in the carrier gas is typically in the range of about 10 ppb to 1000 ppb, and preferably about 10 ppb to 400 ppb.

To provide the necessary level of precision and consistency in the preparation of such primary standard gas mixtures, the apparatus is designed to provide static mixing of one or more liquid or gas components with the carrier gas in a single step.

Figure 1:
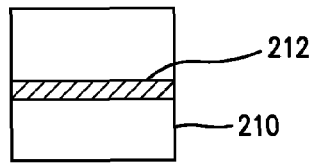
FIG. 1 which illustrates a perspective view of a permeation device.

In the embodiment illustrated in FIG. 1, a permeation device 210 is provided that delivers a known amount of component is provided therein. The permeation device contains a permeation media 212, for example, a polymeric polytetrafluoroethylene tube having a known permeation rate at the operating temperature of the device. Exemplary liquid or gaseous component introduced and diffused through the permeation device include carbon monoxide, carbon dioxide, nitric oxide, dinitrogen oxide, methane, etc. The permeation devices are typically available as the Trace Source™ from Kin-Tek Laboratories, Inc. The gaseous component contacts a membrane and the gas slowly permeates through a membrane at given conditions.

Typical high purity carrier gases, which may be utilized in the apparatus of the present invention include nitrogen, helium, argon, air, oxygen, carbon dioxide, etc. On the other hand, the low concentration liquid or gaseous component (i.e., the analyte) can be chosen from among carbon monoxide, carbon dioxide, nitrous oxide, methane, hydrogen fluoride, hydrogen chloride, and chlorine, hexafluoroethane and sulfur hexafluoride, etc.

Depending on the particular liquid or gaseous component utilized, the permeation device is heated to a predetermined temperature to obtain a constant diffusion rate. Thus, the dispensing time from the permeation device is known and the exact mass of the component diffused from the permeation device can be calculated. If the analyte is in liquid phase, the predetermined temperature is utilized to establish the vapor pressure of the component/analyte and hence the pressure difference across the permeation media to obtain a constant diffusion rate.

On the other hand, if the analyte is in vapor phase, a supply cylinder (not shown) is provided upstream of the permeation device, and the pressure of the component delivered to the permeation device is held at a predetermined level to establish a constant pressure difference across the permeation on media so as to obtain a constant diffusion rate. The analyte concentration at the end of permeation media 212 is maintained at a low and constant level, preferably near zero, by sweeping the permeated component/analyte with the carrier gas to the product container.

Figure 2:
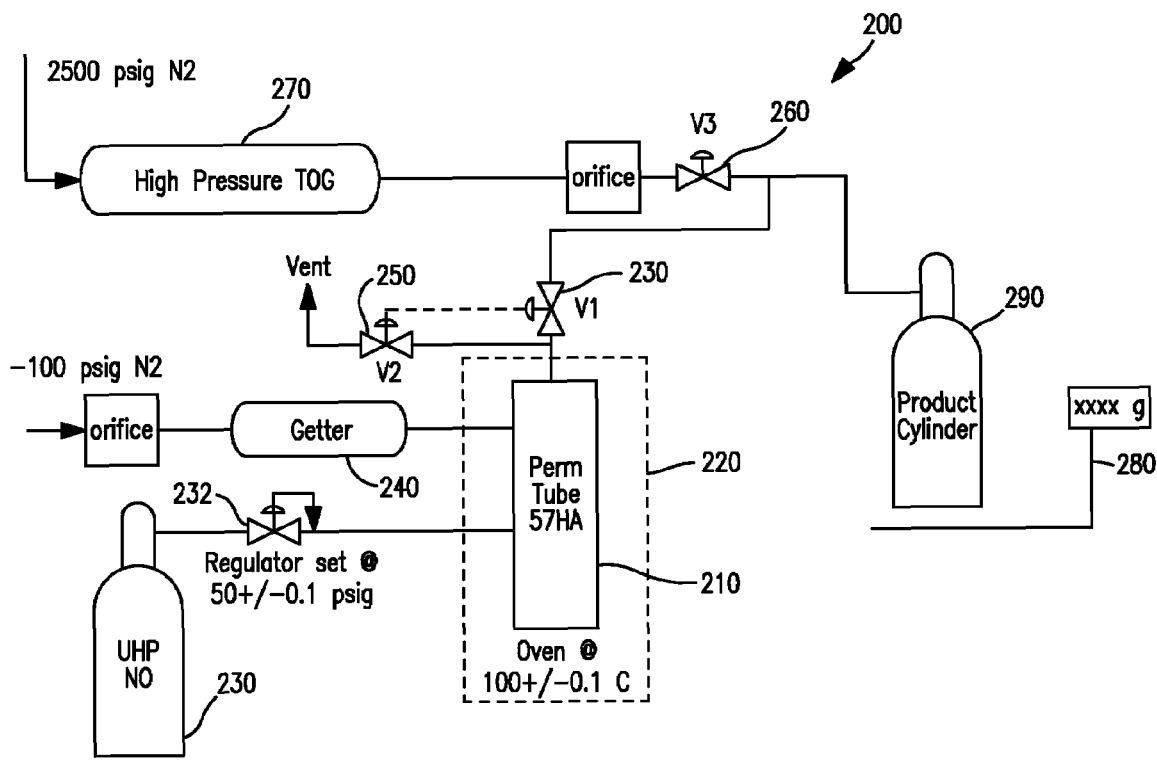
FIG. 2, illustrates schematic view of a system for calibrating standard gas mixtures.

More specifically, and with reference to FIG. 2, a system for producing a primary standard gas mixture, in accordance to another embodiment of the invention is illustrated. The low concentration primary standard gas mixture is generated by blending known amounts of carrier gas and the analyte. System 200 includes at least one permeation device 210 that delivers a known amount of the analyte. Naturally, the permeation device must be calibrated by the manufacturer/vendor to yield a constant known diffusion rate. For this purpose the manufacturer/vendor will fill the device with the component, weigh it, heat it to a constant temperature and maintain it for a known time, then remove it and weigh. The weight difference divided by the known time gives the diffusion rate at that temperature.

FIG. 2 is further explained with respect to producing a mixture where the analyte is nitrous oxide. However, it will be understood by those skilled in the art, that this system may be utilized with any of the aforementioned analytes and carrier gases. A source 230 of ultra high purity nitric oxide is disposed upstream of permeation device 210 and in fluid communication therewith. A regulator 232 on the supply line maintains the supply pressure at about 50 psig and fixes the pressure of the nitric oxide supplied to permeation device 210. Permeation device is enveloped in enclosure 220, where permeation device is maintained within a closely monitored enclosure at a temperature of about 100° C. Separately, through a small orifice, nitrogen gas at sufficient flowrate to sweep the component is continuously provided to permeation device 210 through a getter 240 disposed on a line. The getter removes impurities in the carrier gases, which otherwise might react with the analyte. The nitrogen gas added has a negligible effect on the diffusion rate of permeation device 210, as there is only a slight increase in backpressure which results in product cylinder 290. Further, this portion of nitrogen gas provided to permeation device 210, contributes to the balance of ultra high purity nitrogen gas ultimately delivered to the product cylinder.

As the analyte diffuses through permeation device 210, and is conveyed to product cylinder 290 by opening valve 230 and closing valves 250 and 260. Optionally, when permeation device is not in use, valve 230 is closed and valve 250 is opened to vent the analyte. This procedure maintains the stability of the permeation device, and allows for mixtures to be provided on demand (i.e., at the appropriate diffusion rate), while maintaining the loss of analyte to a negligible amount (i.e., in the case of nitric oxide 0.5 g/day or less). These valves may be selected from among any high pressure valves, which would not contaminate the gas passing therethrough.

The mass of analyte delivered to the product cylinder is known gravimetrically, from the known emission rate of the permeation device and the delivery time (the time valve 230 is open). Upon reaching the desired weight in product cylinder 290, valve 230 is closed. Valve 260 is opened and the balance of ultra high purity carrier gas is supplied to product cylinder 290 from the carrier gas supply source 270. The mass of added carrier gas is determined accurately on scale 280. Based on the diffusion rate of the permeation device, the time necessary to deliver the requisite weight of analyte to the product cylinder and the mass of the added balance of carrier gas, the concentration of the final mixture can be calculated. In this regard, the final concentration is determined as follows:

$$c = \frac{t*d}{w} * 10^{-9},$$

where
c=concentration by weight, ppbw
t=time during which valve 230 is open, minutes
d=component diffusion rate, g/minute
w=weight of carrier gas, g The concentration level can be tailored by a factor as high as one hundred by altering the time permeation device 210 is allowed to discharge the analyte to product cylinder 290. In the event a wider concentration range is desired, the operating temperature of permeation device 210 can be changed. This would require a permeation device calibrated at two different temperatures. Alternatively, the permeation device can be modified so as to either increase or decrease the surface area thereof, which would in turn change the permeation characteristics (i.e., diffusion rate) of the device. If the device is in use at one temperature, then it will be heated/cooled to yield a different but known diffusion rate at the second temperature. During this transition period valve 230 will remain closed and valve 250 will be open.

Overall, system 200 may be controlled through the employment of a programmable logic controller (PLC), or a computer. The valve control, the cylinder scale reading may be input to the PLC, and the addition of analyte into the product cylinder timed accurately. Thereafter, the PLC would perform the concentration calculations. In addition, system 200 may be modified, to include a purge line, where moisture and oxygen are monitored. In this instance, for example, the PLC would purge system 200, and by-pass the introduction of analytes into the product cylinder until the contaminant levels reached acceptable levels (i.e., less than 10 ppb). A high pressure source of nitrogen carrier gas, such as tank 270 disposed downstream of the permeation device, provides the balance of gas to product cylinder 290.

The system described above, can be modified in numerous ways. In a further embodiment, for example, the calibrated standard gas mixtures can comprise multi-components or analytes. In order to implement, this system, a number of permeation devices 210 may be provided in parallel. Each device diffuses a particular analyte which is routed to the product cylinder. The operator will monitor the system and ensure that the various analytes do not backflow out of the product cylinder 290 to which they are delivered, either sequentially or simultaneously.

In accordance with another embodiment, system 200 may be configured to dispense the analytes to a number of product cylinders 290 in a sequential manner. Therefore, a number of product cylinders containing the same calibrated standard gas mixture can be generated in an assembly line production manner. To ensure the accuracy, of the calibrated gas mixture can be achieved by placing each product cylinder on an individual scale, in order to determine the balance of carrier gas necessary. It will be recognized that the scale which may be employed include acoustic wave scale and load cell balances, which may be utilized in conjunction with the PLC to control various aspects of the process.

The system described in FIG. 2 of the invention will be further described in detail with reference to the following example, which is, however, not to be construed as limiting the invention.

EXAMPLE

The primary standard gas mixture desire was set to 100 ppb by weight of nitric oxide (NO) in a nitrogen ($N_2$) mixture. The nitric oxide component/analyte was supplied to a permeation device 210 having a diffusion rate of 367 microgram/minute at 100° C. The time necessary to provide 100 ppb of NO analyte into product cylinder 290 was calculated as follows:

The product cylinder holds 300 cuft at NTP. The density of nitrogen is known to be 32.86 g/cuft at NTP.
Therefore, 300 Cuft of $N_2$=9858 g at NTP
ppb wt=gNO/9858 g$N_2$*1E9
g NO=100 ppbw*9858 g $N_2$/1E9
g NO=0.0009858 g or 0.9868 mg or 985.8 micrograms
The permeation device was a 57 HA model having the above stated diffusion rate.

Thus, 985.8 micrograms/367 micrograms/minute=2.687 minutes or 161.22 seconds to provide 100 ppb of analyte to product cylinder.

Upon calculating the time necessary to provide the 100 ppb of analyte into product cylinder 290, the concentration of the calibrated gas mixture was determined.

As a result, the concentration of the final mixture was calculated as follow:

$$c = \frac{t*d}{w} * 10^{-9},$$

where
c=concentration by weight, ppbw
t=time during which valve 230 is open, minutes
d=component diffusion rate, g/minute
w=weight of carrier gas, g Thereafter, the balance of $N_2$ carrier gas was provided, and the calibrating standard gas mixture was formed via a static mix and without diluents.

Clearly, a primary standard gas mixture is provided through a static mix, and without multiple dilutions.

While the invention has been described in detail with reference to specific embodiments thereof, it will become apparent to one skilled in the art that various changes and modifications can be made, and equivalents employed, without departing from the scope of the appended claims.

What is claimed is:

1. A method for making primary standard gas mixtures, comprising the steps of:
    providing an ultra high purity source for a gaseous component;
    communicating the gaseous component via a conduit to a permeation device disposed in a temperature controlled enclosure;
    diffusing the gaseous component through the permeation device and removing a diffused component therefrom;
    delivering the diffused component either to a product cylinder via a conduit for a predetermined period of time or to a vent system where it may be optionally scrubbed; and
    wherein upon delivery of the diffused component to the product cylinder a balance of purified gas is delivered from a high pressure source to the product container in order to obtain a known concentration of component in the standard gas mixture in the product container.

2. A system for producing primary standard gas mixtures, comprising:

a gas permeation device disposed in a temperature controlled enclosure, the gas permeation device having a constant diffusion rate as a function of temperature;

a supply source of gaseous component in communication with the gas permeation device;

a regulator interposed between the supply source and the gas permeation device to control the pressure of the supply source of the gaseous component;

a product container to receive the gaseous component diffused through the gas permeation device; and a supply source of purified gas in communication to the product container to supply the balance of the gas and obtain a known concentration component in the primary standard gas mixture.

3. The system according to claim 2, wherein the temperature controlled enclosure is an oven.

4. The system according to claim 2, further comprising a program logic controller or computer to monitor and control the supply of component, as well as the supply of the balance of purified gas.

5. The system according to claim 4, wherein the program logic controller or computer is employed to effectuate the switch between a flow of the diffused component to the product container and a flow of purified gas to the product container.

6. The system according to claim 2, further comprising, a balance disposed under the product container to measure the weight of the diffused component routed to the product cylinder.

7. A method for making primary standard gas mixtures comprising the steps of:

supplying a regulated flow of a component from a supply source via a regulator to a gas permeation device disposed within a temperature controlled enclosure;

adjusting the temperature of the temperature controlled enclosure to a prescribed temperature wherein the gas permeation device maintains an approximately constant diffusion rate;

routing the diffused component from the gas permeation device to a product container until a desired amount of said component in the product container is reached; and supplying a balance of purified gas to the product container to obtain a prescribed concentration of the component in the standard gas mixture.

8. The method of claim 7, wherein the step of adjusting the temperature in the temperature controlled enclosure further comprises maintaining a constant temperature in the temperature controlled enclosure.

9. The method of claim 7, wherein the component is nitric oxide, and the balance of purified gas is nitrogen.

10. The method of claim 7, wherein the component is selected from the group consisting of carbon monoxide, carbon dioxide, nitrous oxide, methane, hydrogen fluoride, hydrogen chloride, and chlorine, hexafluoroethane and sulfur hexafluoride and mixtures thereof.

11. The method of claim 7, wherein the balance of purified gas is selected from the group consisting of helium, nitrogen, air, oxygen, carbon dioxide and argon and mixtures thereof.

12. The method of claim 7, wherein the prescribed concentration of the component in the primary standard mixture containing purified gas is in the range of about 10 parts per billion to about 1000 parts per billion.

13. The method of claim 7 further comprising the step of supplying a flow of carrier gas to the gas permeation device to aid in the diffusion of the component through the gas permeation device and routing the diffused component from the gas permeation device to the product container.

* * * * *